United States Patent [19]

Tysse

[11] Patent Number: 4,695,253

[45] Date of Patent: Sep. 22, 1987

[54] ORAL EVACUATION DEVICE AND METHOD

[76] Inventor: Thomas M. Tysse, 2415 Pebblebrook, SE., Grand Rapids, Mich. 49506

[21] Appl. No.: 709,891

[22] Filed: Mar. 8, 1985

[51] Int. Cl.$^4$ .............................................. A61C 5/14
[52] U.S. Cl. ..................................... 433/136; 433/96
[58] Field of Search ........................ 433/136, 138, 96

[56] References Cited

U.S. PATENT DOCUMENTS

| | | | |
|---|---|---|---|
| 278,091 | 5/1883 | Burk | 433/136 |
| 674,650 | 5/1901 | Lundborg | 433/93 |
| 730,128 | 6/1903 | Jordan | 433/93 |
| 1,122,086 | 12/1914 | Dunlop | 433/93 |
| 1,579,608 | 4/1926 | Haudenshield | 433/136 |
| 1,930,712 | 10/1933 | Girvin | 433/96 |
| 2,180,249 | 11/1939 | Lempert | 433/136 |
| 2,255,657 | 9/1941 | Freedman | 433/80 |
| 2,507,938 | 5/1950 | Smith | 433/94 |
| 2,644,234 | 7/1953 | Scott | 433/136 |
| 2,791,030 | 5/1957 | Tofflemier | 433/138 |
| 2,823,455 | 2/1958 | Sprague | 433/93 |
| 3,086,289 | 4/1963 | Orsing | 433/96 |
| 3,768,477 | 10/1973 | Anders et al. | 433/140 |
| 3,777,756 | 12/1975 | Lohr | 433/91 |
| 4,240,789 | 12/1980 | Rosenthaler | 433/136 |
| 4,310,308 | 1/1982 | Oien | 433/91 |

*Primary Examiner*—John J. Wilson
*Attorney, Agent, or Firm*—Price, Heneveld, Cooper, DeWitt & Litton

[57] ABSTRACT

An oral evacuation device and method is adapted for use in conjunction with a dam frame and a dam sheet, which overlie an operating area of the patient's mouth on which a selected procedure is to be performed. The oral evacuation device includes a hollow evacuation tube, having a first end shaped to communicate with a source of suction, and a second end which is flexible and has perforations along its length through which materials, such as saliva, debris, and the like are aspirated. The perforated end of the evacuation tube is threaded through two mating apertures in the dam sheet to form a flexible loop on the bottom side of the dam sheet. In use, the shape and orientation of the evacuation tube is adjusted to conform comfortably with the shape and oriientation of the patient's mouth, and extends into a rearward, lower portion of the patient's mouth in which saliva collects. A retainer holds the evacuation tube loop in the selected operating position such that throughout the operating procedure, the evacuation tube automatically and continuously removes saliva and the like directly from the lower portion of the patient's mouth for improved operating efficiency and increased patient comfort.

42 Claims, 7 Drawing Figures

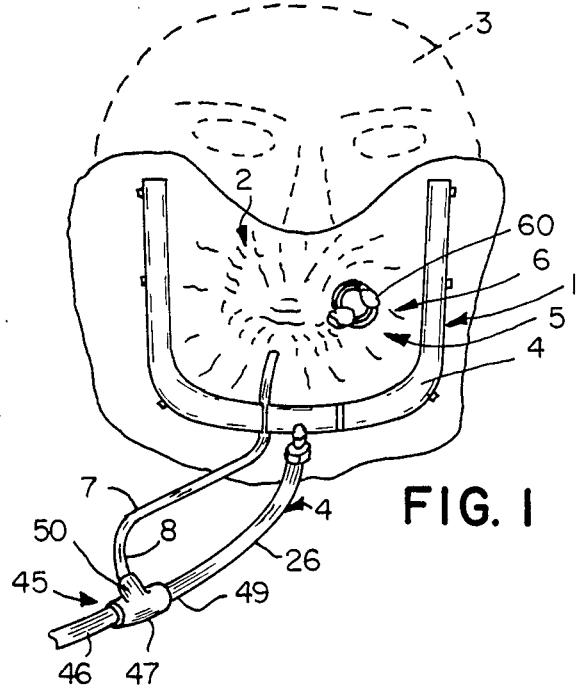
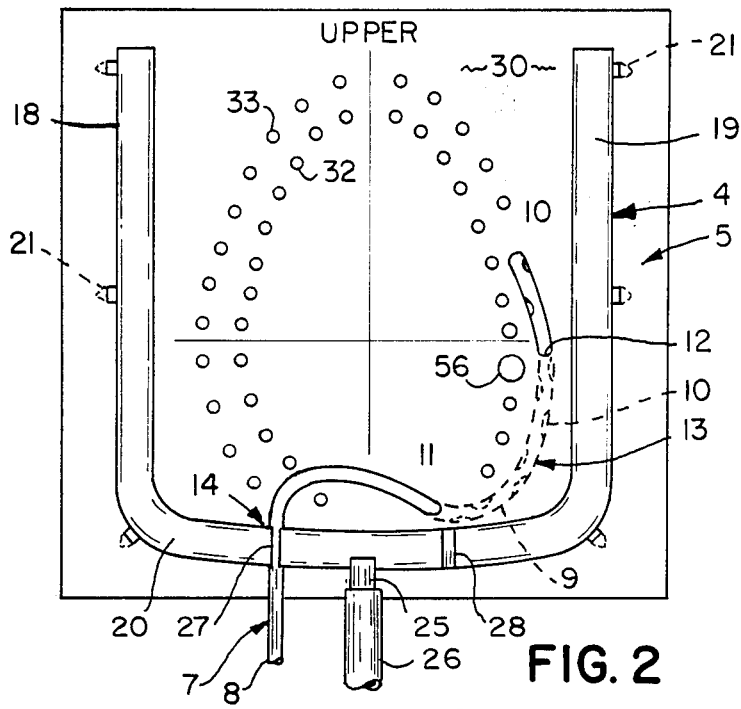
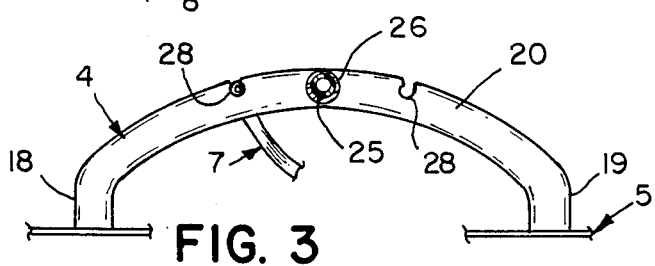
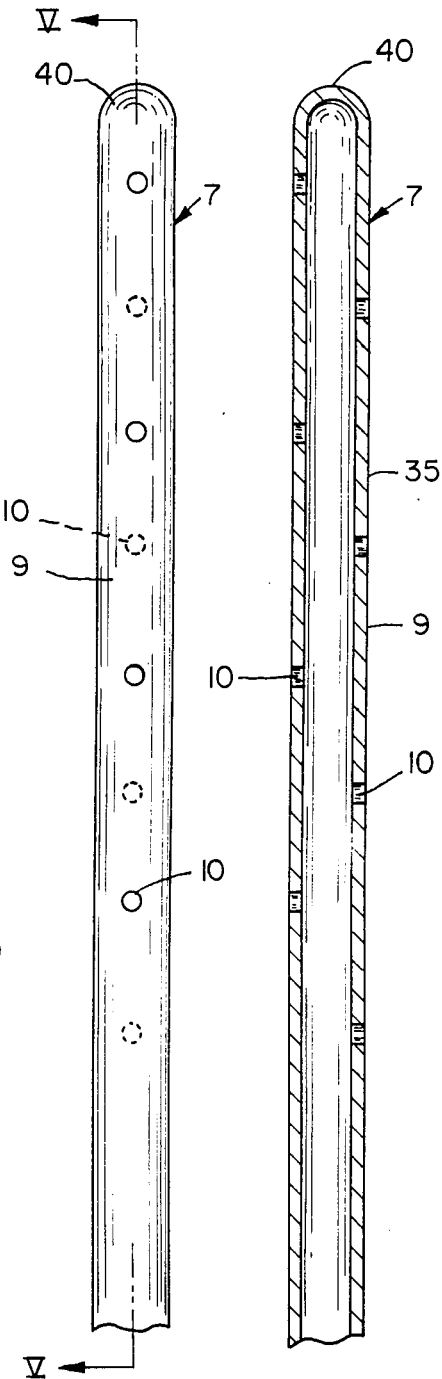
FIG. 1
FIG. 2
FIG. 3
FIG. 4    FIG. 5

ORAL EVACUATION DEVICE AND METHOD

BACKGROUND OF THE INVENTION

The present invention relates to dental tools, appliances, and the like, and more particularly to an oral evacuation device and method.

Oral evacuation devices or aspirators, such as those used in dentistry, oral surgery, and the like are generally well known. Some prior evacuation devices are hung from the mouth of the patient. These devices can interfere with the operating area of the mouth, and are typically considered uncomfortable.

Some aspirators, such as the device illustrated and described in U.S. Pat. No. 4,310,308 to Oien are particularly designed to be used in conjunction with a dental dam, which is frequently used in various operating procedures to isolate a particular area of the patient's mouth on which a certain procedure is to be performed.

Such combination dam and aspirators typically have a relatively large size, and are designed to be used on the cheek side of the teeth, as opposed to the inside or tongue side of the mouth. The evacuation head is attached directly to a conventional suction tube, which is rather stiff, and has a relatively large diameter, such that the tube does not adapt very comfortably to the shape of the patient's mouth. Furthermore, such combination dam and evacuation devices are designed to be used only on the lower half of the patient's mouth, and are not effective in treating areas on the upper half of the patient's mouth. Furthermore, such aspirators typically do not include any type of retainer mechanism that will hold the aspirator in a comfortable position, so as to effectively remove saliva from the back of the patient's mouth throughout the entire operating procedure. An additional drawback associated with prior combination aspirators and dental dams is that the suction on the opposite sides of the dam is at the same general location in the patient's mouth. Hence, when an operating procedure is being performed on a forward portion of the patient's mouth, a large quantity of saliva can collect in the back of the patient's mouth before it rises to a level at which the lower aspirator will begin to function. Since this amount of saliva generally causes patient discomfort, the operating procedure must be interrupted periodically to manually evacuate under the dam. Manual evacuation of the patient's mouth requires the services of a dental assistant throughout the entire operating procedure, and such interruptions greatly increase the time required to complete the operation, which typically results in more cost, and additional patient discomfort.

SUMMARY OF THE INVENTION

One aspect of the present invention is to provide an oral evacuation device and method, which includes a hollow evacuation tube that comfortably and efficiently removes saliva from the patient's mouth throughout the entire operating procedure. The evacuation tube has a first end shaped to communicate with the source of suction or vacuum, and a second end which is flexible, and has perforations along its length through which materials are aspirated. The perforated end of the evacuation tube is adapted to be threaded through two mating apertures in a flexible sheet to form a flexible loop on the bottom side of the sheet. The shape and orientation of the evacuation tube loop is adjusted to conform with the shape and orientation of the patient's mouth, and extends rearwardly into a rearward, lower portion of the patient's mouth in which saliva collects. A retainer holds the evacuation tube loop in the selected shape and orientation, such that during the operating procedure the evacuation tube automatically and continuously removes saliva, and the like directly from the lower portion of the patient's mouth for improved operating efficiency and increased patient comfort.

Preferably, the evacuation tube is used in conjunction with a standard dental dam, which is placed over the patient's mouth and isolates a specific operating area of the same on which a selected procedure is to be performed. When the free end of the evacuation tube is pulled through the upper side of the dam sheet, the evacuation tube simultaneously evacuates saliva and debris from both the top and bottom sides of the dam. In the preferred embodiment of the present invention, the evacuation tube has a predetermined length which permits the device to be used on either the upper half or the lower half of the patient's mouth. A separate suction supply tube and stabilizer arrangement may be provided to prevent forces which act on the supply tube from being transmitted to the evacuation tube, thereby securely retaining the evacuation tube in the selected operating position.

The evacuation device is supported by the dam and the dam frame, and not by the mouth of the patient to prevent interference with the operating area, and provide additional patient comfort. The dam supported evacuation tube arrangement allows comfortable extention of the evacuation device into the critical posterior areas of the mouth, which is not possible with conventional hook-type aspirators.

The principal objects of the present invention are to provide a highly efficient oral evacuation device that has an extremely uncomplicated construction, and is disposable. The evacuation device includes a flexible evacuation tube that fits comfortably in the mouth of the patient, and efficiently evacuates saliva from the patient's mouth throughout the entire operating procedure to minimize interruptions, and to free the assistant to perform other important tasks. The evacuation device can be used on either the upper or lower halves of the patient's mouth without any modification to the basic structure. The evacuation device is efficient in use, economical to manufacture, and particularly well adapted for the proposed use.

These and other features, advantages and objects of the present invention will be further understood and appreciated by those skilled in the art by reference to the following specification, claims and appended drawings.

FIG. 1 is a front perspective view of an oral evacuation device embodying the present invention, shown positioned in the mouth of a patient.

FIG. 2 is a top plan view of the evacuation device, particularly showing a dam frame, a dam sheet, and an evacuation tube in an assembled condition.

FIG. 3 is a fragmentary end elevational view of the evacuation device.

FIG. 4 is an enlarged, fragmentary, plan view of the evacuation tube.

FIG. 5 is an enlarged, fragmentary cross-sectional view of the evacuation tube, taken along the line V—V of FIG. 4.

DETAILED DESCRIPTION OF THE PREFERRED EMBODIMENTS

Figure 6:
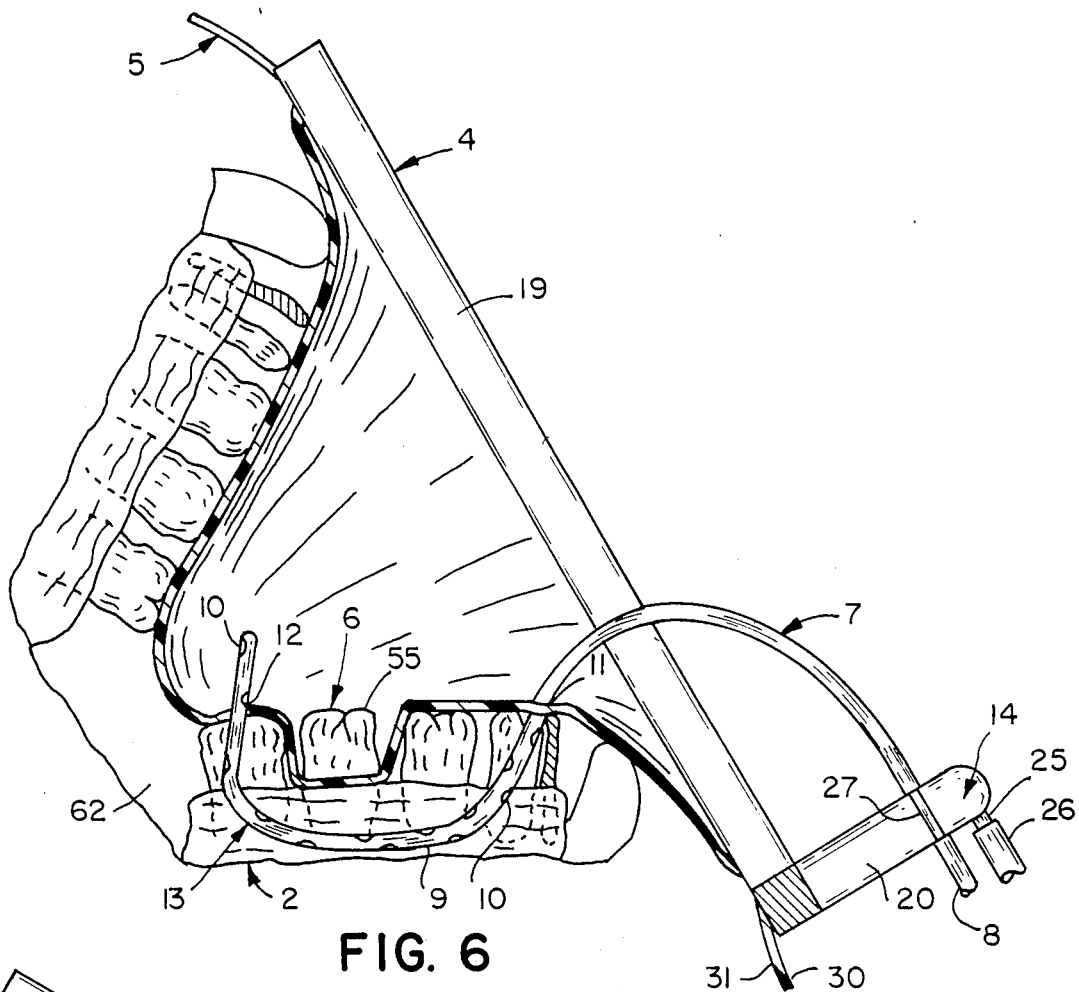
FIG. 6 is a partially schematic, vertical cross-sectional view of the evacuation device, shown positioned for working on a tooth in the lower half of the patient's mouth.

For purposes of description herein, the terms "upper," "lower," "right," "left," "rear," "front," "vertical," "horizontal," and derivatives thereof shall relate to the invention as oriented in FIGS. 1–6 and 7. However, it is to be understood that the invention may assume various alternative orientations and step sequences, except where expressly specified to the contrary.

The reference numeral 1 (FIG. 1) generally designates an oral evacuation device embodying the present invention. In FIG. 1, oral evacuation device 1 is shown in a selected operating position in the mouth 2 of a patient 3. Oral evacuation device 1 is adapted to be used in conjunction with a dam frame 4 and a dam sheet 5, which overlie an operating area 6 of a patient's mouth 2 on which a selected operating procedure is to be performed. Oral evacuation device 1 includes a hollow evacuation tube 7, having a first end 8 shaped to communicate with a source of suction or vacuum (not shown), and a second end 9 (FIG. 2) which is flexible, and has perforations or apertures 10 along its length through which materials, such as saliva and debris are aspirated. The perforated end 9 of evacuation tube 7 is threaded through two mating apertures 11 and 12 in dam sheet 5 to form a flexible loop 13 on the bottom side of dam sheet 5. The shape and orientation of evacuation tube loop 13 is adjusted to conform with the shape and orientation of the patient's mouth 2, and extends into the rearward, lower portion of the patient's mouth in which saliva collects. A retainer 14 holds evacuation tube loop 13 in the selected shape and orientation, such that throughout the operating procedure, evacuation device 1 automatically and continuously removes saliva and the like directly from the lower portion of the patient's mouth 2 for improved operating efficiency and increased patient comfort.

The major portions of dam frame 4 and dam sheet 5 have a construction which is largely conventional, except for those novel features noted hereinafter. Dam frame 4 has a U-shaped top plan configuration, and includes parallel arms 18 and 19, and connecting arm 20 extending laterally therebetween. As best illustrated in FIG. 3, connecting arm 20 has a generally arcuate end elevational shape, which permits dam frame 4 to fit comfortably over the mouth 2 of patient 3. Dam frame arms 18 and 19 each include three outwardly protruding connector pins or stakes 21, which are adapted to engage and attach dam sheet 5 to dam frame 4. Dam frame 1 is typically integrally molded in one piece from a suitable synthetic resin material, such as nylon or the like.

The dam holder or frame 4 of the present evacuation device 1 includes a unique stabilizer pin 25 mounted centrally in the side face of connecting arm 20 which extends forwardly, or away from arms 18 and 19, in a generally perpendicular relationship with connector arm 20. Stabilizer pin 25 is rigid, and in this example comprises a hollow stud. The rearward end of stabilizer pin 25 is rigidly and fixedly mounted in frame connector arm 20, and the forward end of stabilizer pin 25 is adapted for connection with a stabilizer tube 26, as described in greater detail hereinafter.

In the present invention, connecting arm 20 also includes at least one retainer 14, in which evacuation tube 7 is securely held in place throughout the operating procedure. The illustrated dam frame 4 includes two slots 27 and 28, which are positioned on opposite sides of stabilizer pin 25, and form a snap lock with evacuation tube 7. As best illustrated in FIG. 3, snap lock slots 27 and 28 have a generally arcuate end elevational shape, with an angular measure somewhat greater than 180 degrees. The inside diameter of snap lock slots 27 and 28 is dimensioned so as to closely receive the evacuation tube 7 therein, and frictionally abut against the exterior surface of evacuation tube 7 to hold the same in place. In one specific working sample of the present invention, snap lock slots have a diameter in the nature of 0.11 inch, an upper opening width of 0.11 inch, and are oriented in a parallel relationship with each other, as well as frame arms 18 and 19.

As best shown in FIG. 2, the illustrated dam sheet 5 has a substantially square top plan configuration, and is constructed from a thin membrane of resiliently flexible material, such as rubber, synthetic resin material, or the like. Dam sheet 5 has top and bottom sides 30 and 31 respectively, and is adapted to stretch over dam frame 4 and be retained thereon by stakes 21. Dam sheet 5 includes a first set of indicia 32 arranged in a pattern generally corresponding to a typical tooth pattern to locate the operating area 6 of the patient's mouth 2. Dam sheet 5 further includes a second set of indicia 33, which is spaced in a predetermined relationship with the first set of indicia 32, as described in greater detail hereinafter, to locate evacuation tube apertures 10 and 11. In this example, indicia 32 and 33 each comprises a set of circles or dots that are printed on the top side 30 of dam sheet 5 in a generally arcuate or oval pattern. Indicia 32 and 33 are concentric, with the forward and rearward sets of dots corresponding to the upper and lower halves of the mouth respectively. Each dot in second indicia 33 is radially aligned with, and disposed directly behind a corresponding dot in the first indicia 32, for purposes to be described in detail below.

In the illustrated embodiment of the present invention, evacuation tube 7 comprises a single piece of resiliently flexible tubing constructed from a synthetic resin material. Evacuation tube 7 preferably has a length sufficient to adjust the size and shape of evacuation tube loop 13 to work on an operating area located on either the upper half or the lower half of the patient's mouth 2. Evacuation tube 7 has a substantially uniform lateral cross-sectional shape along its entire length, and its free end 40 is closed. It is to be understood that the free end 40 of evacuation tube 7 may be open to increase evacuation on the top side 30 of dam sheet 5. Aspirating apertures 10 are preferably spaced uniformly along the length of the perforated end 9 of evacuation tube 7, and in the illustrated example are positioned alternately on opposite sides of the evacuation tube to maximize evacuating efficiency. In one working embodiment of the present invention, evacuation tube 7 is constructed of a thin, lightweight tubing known in the trade as Tygon B-44-3, and has an overall length of 6 to 10 inches, wherein the perforated end 9 is approximately 3½ inches long. The inside diameter of the referenced working embodiment of evacuation tube 7 is approximately 1/16 inch, and the outside diameter is approximately ⅛ inch, such that the sidewall thickness is around 1/32 inch. In the referenced example, asperating apertures 10 have a diameter in the range of 1/32 to 3/32 inch, and are spaced apart a distance in the range of ⅛ to ⅜ inch.

Evacuation device 1 preferably includes a stabilizer 45 (FIGS. 1 and 2) to securely retain flexible loop 13 in its selected operating position throughout the entire operating procedure. In the illustrated example, a separate suction supply tube 46 is provided, along with a T-fitting 47. T-fitting 47 includes opposite, aligned legs 48 and 49, and a perpendicular extending leg 50. One end of suction supply tube 46 is attached to leg 48 of T-fitting 47, and the opposite end of suction supply tube 46 is adapted to communicate with the source of vacuum or suction (not shown). Stabilizer tube 26 has one end connected with stabilizer pin 25 on dam sheet 5, and the opposite end is connected with leg 49 of T-fitting 47. The open end of evacuation tube 7 is connected with leg 50 of T-fitting 47, such that during operation, any forces that act on suction supply tube 46 are transmitted directly to dam frame 4, and are not transmitted to evacuation tube 7. In this manner, once the correct position of evacuation tube 7 has been set in the patient's mouth, it will not inadvertently be knocked out of the operating position. In the referenced working example of the present invention, stabilizer tube 26 and suction supply tube 46 are constructed from lengths of plastic tubing, having an inside diameter of approximately ⅛ inch, and an outside diameter of around ¼ inch. The exemplary stabilizer tube 26 has a length in the range of 2½ to 3½ inches. Stabilizer tube 26 effectively closes off or seals the arm 49 of T-fitting 47, so that the suction is communicated through T-fitting 47 directly to evacuation tube 7.

As will be apparent to those skilled in the art, oral evacuation device 1 can be used in operating procedures that do not require actual isolation of that area of the patient's mouth 2 on which the operating procedure is to be performed. In such non-isolating operating procedures, a suitable dam frame 4 and dam sheet 5 are positioned over and retained in the patient's mouth, and function to simply position evacuation tube 7 properly in the mouth of patient 3 for efficient evacuation. However, dam frame 4 and dam sheet 5 do not, under such circumstances, serve to actually isolate the operating area of the patient's mouth. Hence, the meaning of the terms "dam frame" and "dam sheet," as used herein, is not intended in any way to limit the scope of the present invention to applications in which the operating area is actually isolated, except as the claims expressly state otherwise.

Oral evacuation device 1 can be used in conjunction with a wide variety of different types of oral operating procedures, including oral surgery, dentistry and the like. In the examples illustrated in FIGS. 1, 6 and 7, evacuation device 1 is shown being used in a dental application, wherein a selected procedure is to be performed upon a single tooth 55 in the patient's mouth 2. The method for adapting evacuation device 1 to this particular procedure, and like procedures, is set forth hereinbelow. However, it is to be understood that the following method description is merely exemplary of one application of evacuation device 1, and should not be considered limiting.

Dam sheet 5 is first stretched over and mounted on dam frame 4 with indicia 29 and 30 oriented upwardly, and positioned centrally between the arms 18 and 19 of dam frame 4. A first hole or aperture 56 (FIGS. 1 and 2) is formed in dam sheet 5 at a location that corresponds to the patient's tooth 55 on which the selected procedure is to be performed. The dots in first indicia 32 assist the dentist in locating the tooth hole 56 in dam sheet 5 in a conventional fashion. The dentist then forms evacuation tube apertures 11 and 12 in dam sheet 5. The dots of second indicia 33 assist the dentist in locating the evacuation apertures 11 and 12 in the following fashion. The first dam sheet aperture 11 is located on the lower half of the patient's mouth 2, preferably at a forward portion thereof, directly behind the lower front teeth of the patient. The dentist locates the indicia dots 32 on dam sheet 5 which correspond to the lower front teeth of the patient, and then forms the first aperture 11 therein at a position slightly behind the subject indicia, toward the indicia corresponding to the "upper" half of the teeth indicia 32, as shown in FIGS. 1-2 and 6-7.

The second dam sheet aperture 12 is preferably positioned immediately behind the tooth hole 56. Experience presently indicates that effective evacuation on both sides of dam sheet 5 can be accomplished by positioning the second dam sheet aperture 12 approximately ½ inch directly behind tooth hole 56. Hence, the second indicia dots 33 are spaced directly behind the corresponding teeth dots 32 a distance of approximately ½ inch. Thus, once the dentist locates where tooth hole 56 is to be positioned, in a conventional fashion, he can easily locate evacuation tube aperture 12 at that one of the second indicia dots 30 which is located directly behind the corresponding tooth indicia 29 or aperture 56. Both dam sheet apertures 11 and 12 are generally circular in shape and are sized to closely receive evacuation tube 7 therethrough. Each of the apertures 56, 11 and 12 in dam sheet 5 may be formed by a conventional punch, or the like.

The free end 40 of evacuation tube 7 is then threaded through dam sheet apertures 10 and 11 in the following fashion. The evacuation tube free end 40 is first inserted through aperture 11 from the top side 30 of dam sheet 5. Next, a length of evacuation tube, in the range of 1 to 2½ inches is then pulled through dam sheet 5, and the free end 40 of evacuation tube 7 is then inserted through aperture 12, from the bottom side 31 of dam sheet 5. Preferably, the free end 40 of evacuation tube 7 is pulled through the top side 30 of dam sheet 5 a distance in the nature of ¼ to ½ inch to position at least one or two aspirating apertures 10 on the top side 30 of the dam sheet, so that saliva and debris can be evacuated simultaneously from both sides of dam sheet 5. That portion of evacuation tube 7 disposed on the bottom side 31 of dam sheet 5 forms flexible loop 13. When working on the bottom of the patient's mouth 2, flexible loop 13 is preferably adjusted to an initial length of approximately 1½ inches. When working on the upper half of the patient's mouth 2, flexible loop 13 is preferably adjusted to an initial length of approximately 2 inches. Since the final adjustment of flexible loop 13 is not made until evacuation device 1 is placed in the patient's mouth 2, the initial adjustment of flexible loop 13 is not critical.

Oral evacuation device 1 is then placed in the patient's mouth 2 in the following manner. A conventional dam clip 60 is attached to dam sheet 5 over tooth hole 56. Dam sheet 5 is then placed over the patient's mouth, and dam sheet tooth hole 56 is positioned over the tooth 55 of the patient on which the operating procedure is to be performed. Dam clip 60 is attached to tooth 55, so as to securely hold dam sheet 5 and dam frame 4 in position with respect to the mouth 2 of patient 3.

Figure 7:
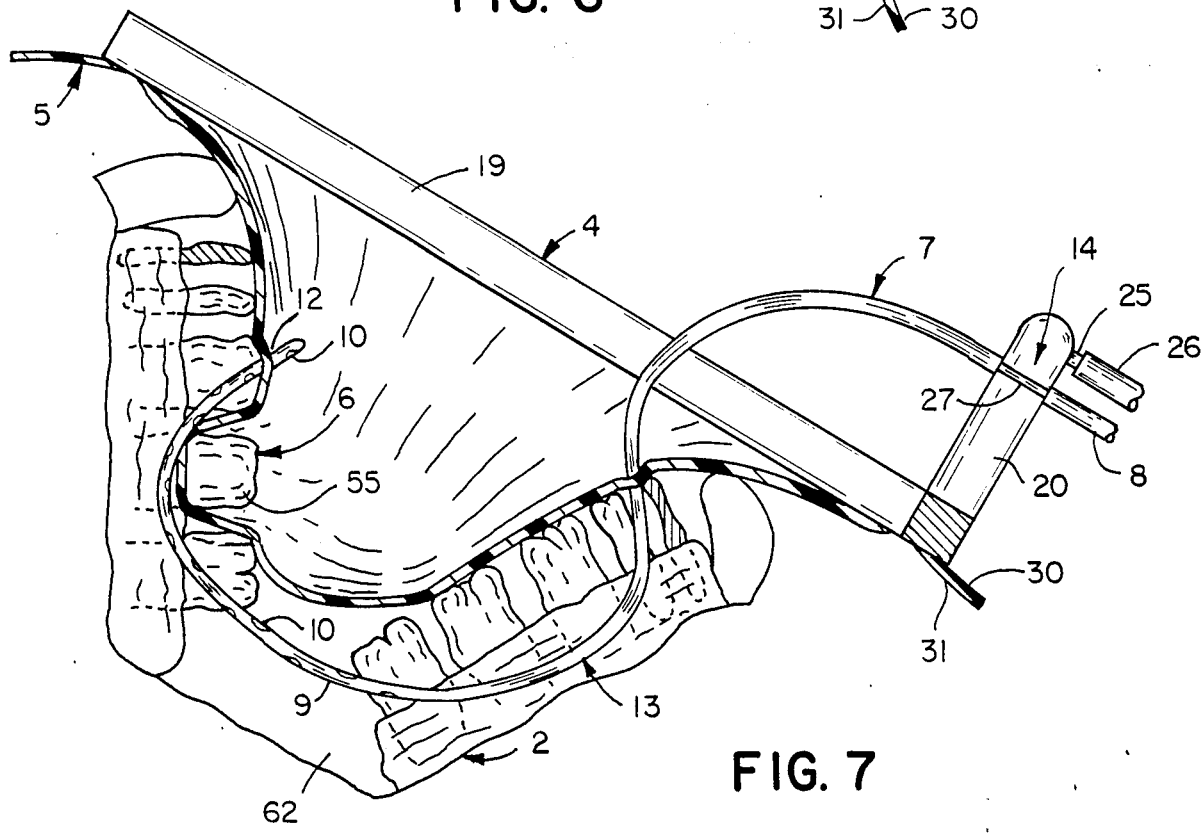
FIG. 7 is a partially schematic, vertical cross-sectional view of the evacuation device, shown positioned for working on a tooth located in the upper half of the patient's mouth.

Evacuation tube 7 is then adjusted to the final operating position to achieve maximum patient comfort, as well as efficient evacuation. In the preferred operating position, flexible loop 13 conforms with the shape and orientation of the patient's mouth, wherein evacuation tube 7 extends downwardly and rearwardly from dam sheet aperture 11 into and along the tongue side of the patient's mouth 2 to a rearward, lower portion 62 of the patient's mouth 2 in which saliva collects, and thence upwardly through the second dam sheet aperture 12. FIG. 6 illustrates an exemplary operating position for flexible loops 13, when working on the lower half of the patient's mouth 2. FIG. 7 illustrates an exemplary operating position for evacuation tube 7, when working on the upper half of the patient's mouth 2. In both examples, the flexible evacuation tube 7 conforms automatically and comfortably to the shape of the patient's mouth. The dentist adjusts the shape and orientation of flexible loop 13 into its final operating position by axially twisting or rotating evacuation tube 7, and also by extending and retracting evacuation tube 7 through dam sheet aperture 11. Because aspirating apertures 10 are positioned alternately on opposite sides of evacuating tube 7, the axial rotation and position of evacuating tube 7 does not adversely effect evacuating efficiency. Since the flexible loop 13 is supported wholly by the dam sheet 5 and dam frame 4, there is no weight placed upon the tissue of the patient's mouth, as experienced with prior hook-shaped evacuation devices that are hung from the patient's mouth.

Once the proper operating position for loop 13 has been achieved, evacuation tube 7 is securely retained in the selected position by inserting the outer end of evacuation tube 7 into one of the two snap lock slots 27 and 28 on dam frame 4. For extra stability, evacuation tube 7 is preferably inserted in that one of snap lock slots 27 and 28 which is located on the side of the patient's mouth 2 opposite to the operating area 6, which in the illustrated example is slot 27. Suction supply tube 46 is then connected to a source of vacuum or suction (not shown), and stabilizer 45 is assembled with the outer end of evacuation tube 7 connected with leg 50 of T-fitting 47. In the event that suction supply tube 46 is inadvertently pulled or knocked by the patient, the dental assistant, or the like, such forces are not transmitted to evacuation tube 7, and will therefore not move evacuation tube 7 from its finally adjusted, operating position.

During the operating procedure, saliva and the like which collect in the lower portion 62 of the patient's mouth 2 is automatically and continuously evacuated through the aspirating apertures 10 in the flexible loop portion 13 of evacuating tube 7. On the top side 30 of dam sheet 5, debris, drill water, and the like are continuously evacuated through the aspirating apertures 10 adjacent the free end 40 of evacuation tube 7.

When the operating procedure is finished, oral evacuation device 1 is removed from the patient's mouth 2. Because of the uncomplicated design of evacuation tube 7, it can be economically manufactured, such that evacuation tube 7 can simply be discarded, along with dam sheet 5. A new, sterile evacuation tube 7 is then used for each operating procedure.

Oral evacuation device 1 provides maximum evacuation efficiency on both the top and bottom sides of dam sheet 5, such that the operating procedure need not be interrupted to manually evacuate the patient's mouth 2, and the dental assistant is thereby freed to perform other important tasks. The flexible nature of evacuation tube 7 makes it extremely comfortable for the patient, and efficient in operation. Evacuation device 1 is easily adapted to be used on either the upper or lower half of the patient's mouth. The uncomplicated nature of oral evacuation device 1 is such that it can be economically manufactured, which not only minimizes expense, but also adapts the device to be disposible, so that a new, sterile device can be used for each operating procedure.

In the foregoing description, it will be readily appreciated by those skilled in the art that modifications may be made to the invention without departing from the concepts disclosed herein. Such modifications are to be considered as included in the following claims, unless these claims by their language expressly state otherwise.

The embodiments of the invention in which an exclusive property or privilege is claimed are defined as follows:

1. An oral evacuation device, comprising:
   a frame shaped to fit over at least a portion of the mouth of a patient;
   a flexible sheet stretched over said frame, having top and bottom sides, and shaped to cover at least a portion of the patient's mouth;
   means for positioning said sheet over an operating area of the patient's mouth on which a selected procedure is to be performed;
   means for releasably retaining said sheet in a selected position with respect to the operating area of the patient's mouth;
   an evacuation tube, having a hollow body with a sidewall, and first and second ends; the first end of said evacuation tube being shaped for communication with a source of suction, and the second end of said evacuation tube having a plurality of apertures, which are spaced along the length thereof, and extend through the sidewall of said evacuation tube for aspirating materials therethrough;
   first and second apertures disposed in said sheet through which the second end of said evacuation tube is threaded to form a flexible loop on the bottom side of said sheet;
   said second end of said evacuation tube being resiliently flexible to permit adjusting the shape and orientation of said evacuation tube loop into an operating position that conforms with the shape and orientation of the patient's mouth by extending downwardly from said first sheet aperture into and along the tongue side of the patient's mouth to a rearward, lower portion of the patient's mouth in which saliva collects, and thence upwardly through said second sheet aperture; and
   means for releasably retaining said evacuation tube loop in the operating position, whereby throughout the operating procedure, said evacuation tube automatically and continuously removes saliva, and the like directly from the lower portion of the patient's mouth for improved operating efficiency and increased patient comfort.

2. A device as set forth in claim 1, wherein:
   said frame comprises a dam frame;
   said sheet comprises a dam sheet; and
   said dam sheet includes a third aperture therethrough, which is positioned and shaped to fit over the operating area of the patient's mouth and at least partially isolate the same.

3. A device as set forth in claim 2, wherein:

said evacuation tube includes a free end extending through said second dam sheet aperture on the top side of said dam sheet; and said free end of said evacuation tube includes at least one aperture through the sidewall thereof, whereby saliva and debris are simultaneously evacuated from both the top and bottom sides of said dam sheet.

4. A device as set forth in claim 3, wherein:
said evacuation tube has a length sufficient to adjust the size and shape of said evacuation tube loop to work on operating areas located on both the upper and lower halves of the patient's mouth.

5. A device as set forth in claim 4, wherein:
said evacuation tube retaining means comprises a snap lock on said dam frame which releasably engages with an outer surface of said evacuation tube.

6. A device as set forth in claim 5, wherein said evacuation tube retaining means further comprises:
a suction supply tube having one end adapted for connection with the source of suction, and the other end operably communicating with the first end of said evacuation tube; and
a stabilizer physically connecting said suction supply tube with said dam frame, whereby forces acting on said suction supply tube are not transmitted to said evacuation tube.

7. A device as set forth in claim 6, wherein:
said dam frame includes a second snap lock positioned in a laterally spaced apart relationship with said first named snap lock.

8. A device as set forth in claim 7, wherein:
said evacuation tube is positioned in that one of said first and second named snap locks located on the side of the patient's mouth opposite to the operating area.

9. A device as set forth in claim 8, wherein:
said evacuation tube is adapted for longitudinally extending and retracting said evacuation tube through said first dam sheet aperture.

10. A device as set forth in claim 9, wherein:
said evacuation tube is adapted for axially rotating said evacuation tube with respect to the patient's mouth.

11. A device as set forth in claim 10, including:
a first set of indicia on said dam sheet arranged in a pattern generally corresponding to a typical tooth pattern to locate said third dam sheet aperture; and
a second set of indicia on said dam sheet, spaced in a predetermined pattern and relationship with said first set of indicia to locate said first and second dam sheet apertures.

12. A device as set forth in claim 11, wherein:
said dam sheet retaining means comprises a conventional dam clip.

13. A device as set forth in claim 12, wherein:
said evacuation tube second end has a length in the range of 2½ to 4½ inches.

14. A device as set forth in claim 13, wherein:
said evacuation tube apertures are spaced substantially uniformly along the second end of said evacuation tube, and are generally circular in shape with a diameter in the range of 1/32–3/32 inch.

15. A device as set forth in claim 14, wherein:
said evacuation tube apertures are spaced apart a distance in the range of ⅛–⅜ inch.

16. A device as set forth in claim 15, wherein:

said evacuation tube has an inside diameter of 1/16 inch and an outside diameter of ⅛ inch.

17. A device as set forth in claim 1, wherein:
said evacuation tube has a length sufficient to adjust the size and shape of said evacuation tube loop to work on operating areas located on both the upper and lower halves of the patient's mouth.

18. A device as set forth in claim 1, wherein:
said evacuation tube retaining means comprises a snap lock on said frame which releasably engages with the outer surface of said evacuation tube.

19. A device as set forth in claim 1, wherein said evacuation tube retaining means comprises:
a suction supply tube having one end adapted for connection with the source of suction, and the other end operably communicating with the first end of said evacuation tube; and
a stabilizer physically connecting said suction supply tube with said dam frame, whereby forces acting on said suction supply tube are not transmitted to said evacuation tube.

20. A device as set forth in claim 1, wherein:
said evacuation tube is adapted for longitudinally extending and retracting said evacuation tube through said first dam sheet aperture.

21. A device as set forth in claim 1, wherein
said evacuation tube is adapted for axially rotating said evacuation tube with respect to the patient's mouth.

22. A device as set forth in claim 1, including:
a first set of indicia on said dam sheet generally corresponding to a typical tooth pattern to locate said first dam sheet aperture; and
a second set of indicia on said dam sheet, spaced in a predetermined pattern and relationship with said first set of indicia to locate said second and third dam sheet apertures.

23. A device as set forth in claim 1, wherein:
said evacuation tube second end has a length in the range of 2½ to 4½ inches; and
said evacuation tube apertures are spaced substantially uniformly along the second end of said evacuation tube, and are generally circular in shape with a diameter in the range of 1/32–3/32 inch.

24. A device as set forth in claim 23, wherein:
said evacuation tube apertures are spaced apart a distance in the range of ⅛–⅜ inch; and
said evacuation tube has an inside diameter of 1/16 inch and an outside diameter of ⅛ inch.

25. A method for oral evacuation and isolation, comprising the steps of:
providing a dam having a dam frame with a flexible dam sheet stretched thereover;
forming a first aperture in the dam sheet with a predetermined size and location to fit over, and at least partially isolate an operating area of the patient's mouth on which a selected procedure is to be performed;
providing an evacuation tube, having a hollow body with a sidewall, and first and second ends; the first end of the evacuation tube being shaped for communication with a source of suction, and the second end of the evacuation tube being flexible and having a plurality of apertures, which are spaced along the length thereof, and extend through the sidewall of the tube for aspirating materials therethrough;

forming a second aperture in the dam sheet at a predetermined location, which in operation is adjacent to a forward, lower portion of the patient's mouth; the second dam sheet aperture being sized to closely receive an associated portion of the evacuation tube therethrough;

forming a third aperture in the dam sheet at a predetermined location adjacent to and generally behind the first dam sheet aperture, which in operation is adjacent to a rearward, lower portion of the patient's mouth, the third dam sheet aperture being sized to closely receive an associated portion of the evacuation tube therethrough;

threading the second end of the evacuation tube through the second and third dam sheet apertures, and forming a flexible loop therefrom on a bottom side of the dam sheet;

inserting the dam and evacuation tube over and into the mouth of the patient, and positioning the first dam sheet aperture over the operating area of the patient's mouth to at least partially isolate the same;

releasably retaining the dam sheet in a selected position with respect to the operating area of the patient's mouth;

adjusting the shape and orientation of the evacuation tube into an operating position which conforms comfortably with the shape and orientation of the patient's mouth, so that the evacuation tube second end extends downwardly from the second dam sheet aperture into and along the tongue side of the patient's mouth to a rearward, lower portion of the patient's mouth in which saliva collects, and thence upwardly through the third dam sheet aperture;

releasably retaining the evacuation tube loop in the operating position; and communicating the first end of the evacuation tube with a source of suction, whereby during the operating procedure the evacuation tube automatically and continuously removes saliva, and the like directly from the lower portion of the patient's mouth for improved operating efficiency and increased patient comfort.

26. A method as set forth in claim 25, including:
inserting the free end of the evacuation tube through the third dam sheet aperture a distance sufficient to position at least one of the aspirating apertures on the top side of the dam sheet, whereby saliva and debris are simultaneously evacuated from both the top and bottom sides of the dam sheet.

27. A method as set forth in claim 26, wherein:
said evacuation tube loop adjusting step comprises longitudinally extending and retracting the evacuation tube through the second dam sheet aperture.

28. A method as set forth in claim 27, wherein:
said evacuation tube loop adjusting step further comprises axially rotating the evacuation tube with respect to the patient's mouth.

29. A method as set forth in claim 28, wherein:
said evacuation tube adjusting step is performed after the dam and evacuation tube inserting step, while the evacuation tube is positioned in the patient's mouth.

30. A method as set forth in claim 29, wherein:
said evacuation tube retaining step comprises snapping the evacuation tube into a snap lock on the dam frame.

31. A method as set forth in claim 30, wherein said evacuation tube retaining step further comprises:
providing a separate suction supply tube with a fitting at a first end thereof;

communicating a second end of the suction supply tube with a source of suction;

communicating the first end of the evacuation tube with the fitting; and physically connecting the fitting to the dam frame, such that forces acting on the suction supply tube are not transmitted to the evacuation tube.

32. A method as set forth in claim 31, wherein:
said evacuation tube retaining step further comprises snapping the evacuation tube onto that side of the dam frame located on the side of the patient's mouth opposite to the operating area.

33. A method as set forth in claim 32, wherein:
said dam sheet retaining step comprises attaching a dam clip to the dam sheet, and placing the dam clip over a tooth at the operating area of the patient's mouth.

34. A method as set forth in claim 33, including:
printing a first set of indicia on the dam sheet in a pattern generally corresponding to a typical tooth pattern to locate the first dam sheet aperture; and printing a second set of indicia on the dam sheet in a predetermined pattern and relationship with the first set of indicia to locate the second and third dam sheet apertures.

35. A method as set forth in claim 25, wherein:
said evacuation tube loop adjusting step comprises longitudinally extending and retracting the evacuation tube through the second dam sheet aperture.

36. A method as set forth in claim 25, wherein:
said evacuation tube loop adjusting step comprises axially rotating the evacuation tube with respect to the patient's mouth.

37. A method as set forth in claim 25, wherein:
said evacuation tube adjusting step is performed after the dam and evacuation tube inserting step, while the evacuation tube is positioned in the patient's mouth.

38. A method as set forth in claim 25, wherein:
said evacuation tube retaining step comprises snapping the evacuation tube into a snap lock on the dam frame.

39. A method as set forth in claim 25, wherein said evacuation tube retaining step comprises:
providing a separate suction supply tube with a fitting at a first end thereof;

communicating a second end of the suction supply tube with the source of suction;

communicating the first end of the evacuation tube with the fitting; and physically connecting the fitting to the dam frame, such that forces acting on the suction supply tube are not transmitted to the evacuation tube.

40. A method as set forth in claim 25, wherein:
said evacuation tube retaining step comprises connecting the evacuation tube onto that side of the dam frame located on the side of the patient's mouth opposite to the operating area.

41. A method as set forth in claim 25, wherein:
said dam sheet retaining step comprises attaching a dam clip to the dam sheet, and placing the dam clip over a tooth at the operating area of the patient's mouth.

42. A method as set forth in claim 25, including:
printing a first set of indicia on the dam sheet in a pattern generally corresponding to the typical tooth pattern to locate the first dam sheet aperture; and printing a second set of indicia on the dam sheet in a predetermined pattern and relationship with the first set of indicia to locate the second and third dam sheet apertures.

* * * * *